United States Patent
Niwa

(10) Patent No.: US 7,664,299 B2
(45) Date of Patent: Feb. 16, 2010

(54) APPARATUS THAT PREPARES INFORMATION RELATING TO IMAGE DATA

(75) Inventor: Kenichi Niwa, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 927 days.

(21) Appl. No.: 11/092,806

(22) Filed: Mar. 30, 2005

(65) Prior Publication Data

US 2005/0219664 A1  Oct. 6, 2005

(30) Foreign Application Priority Data

Apr. 2, 2004  (JP) ............... 2004-110351

(51) Int. Cl.
  *G06K 9/00*  (2006.01)
(52) U.S. Cl. .................... 382/128; 128/920; 382/305; 600/407; 600/425; 705/3
(58) Field of Classification Search .......... 128/920; 382/128, 131, 132, 305; 600/407, 425; 705/2, 705/3; 707/6
See application file for complete search history.

(56) References Cited

U.S. PATENT DOCUMENTS

| | | | | |
|---|---|---|---|---|
| 5,241,472 | A * | 8/1993 | Gur et al. ................. | 382/128 |
| 6,823,203 | B2 * | 11/2004 | Jordan .................... | 600/407 |
| 6,839,455 | B2 * | 1/2005 | Kaufman ................. | 382/128 |
| 6,925,199 | B2 * | 8/2005 | Murao .................... | 382/131 |
| 6,968,077 | B1 * | 11/2005 | Yamanaka ............... | 382/128 |
| 6,990,229 | B2 * | 1/2006 | Ohishi .................... | 382/154 |
| 7,327,866 | B2 * | 2/2008 | Bae et al. ................. | 382/131 |
| 7,426,567 | B2 * | 9/2008 | Wortmann et al. ........ | 709/231 |
| 7,457,672 | B2 * | 11/2008 | Katsman et al. .......... | 700/17 |
| 2002/0065460 | A1 * | 5/2002 | Murao .................... | 600/425 |
| 2003/0156765 | A1 * | 8/2003 | Yamamichi ............... | 382/305 |
| 2004/0027359 | A1 * | 2/2004 | Aharon et al. ............ | 345/619 |
| 2004/0069311 | A1 * | 4/2004 | Sasaki et al. ............. | 128/897 |
| 2004/0086163 | A1 * | 5/2004 | Moriyama et al. ........ | 382/131 |
| 2004/0146190 | A1 * | 7/2004 | Kasai ..................... | 382/128 |
| 2004/0151358 | A1 * | 8/2004 | Yanagita et al. .......... | 382/132 |
| 2004/0186370 | A1 * | 9/2004 | Ishimitsu et al. ......... | 600/407 |

(Continued)

FOREIGN PATENT DOCUMENTS

JP  62-70973  4/1987

(Continued)

OTHER PUBLICATIONS

U.S. Appl. No. 12/062,209, filed Apr. 3, 2008, Minakuchi, et al.

*Primary Examiner*—Gregory M Desire
(74) *Attorney, Agent, or Firm*—Oblon, Spivak, McClelland, Maier & Neustadt, L.L.P.

(57) ABSTRACT

An image storing apparatus for storing at least one image based on an image data generated by an imaging apparatus is provided. The image storing apparatus includes a receiving unit, a processor, and a storage device. The receiving unit is configured to receive the image data. The processor is configured to prepare image-relating information and prepare a data set including the image-relating information and the image data following the image-relating information. The processor prepares leading information leading to the image data as part of the image-relating information. The storage device is configured to store the data set.

30 Claims, 14 Drawing Sheets

U.S. PATENT DOCUMENTS

| | | | |
|---|---|---|---|
| 2004/0190781 A1* | 9/2004 | Shiibashi et al. | 382/210 |
| 2004/0193022 A1* | 9/2004 | Torii et al. | 600/300 |
| 2005/0008262 A1* | 1/2005 | Komiya et al. | 382/305 |
| 2005/0190994 A1* | 9/2005 | Yamanaka | 382/305 |

FOREIGN PATENT DOCUMENTS

| | | |
|---|---|---|
| JP | 10-177642 | 6/1998 |
| JP | 11-284682 | 10/1999 |

* cited by examiner

APPARATUS THAT PREPARES INFORMATION RELATING TO IMAGE DATA

CROSS-REFERENCE TO RELATED APPLICATION

This application is based upon and claims the benefit of priority from prior Japanese Patent Application No. P2004-110351, filed on Apr. 2, 2004, the entire contents of which are incorporated herein by reference.

BACKGROUND OF THE INVENTION

1. Field of the Invention

The present invention relates to an image storing apparatus that prepares a data set including image-relating information and an image data. The present invention also relates to an image display apparatus, an imaging apparatus and an information processing apparatus, each of which prepares a data set including image-relating information and an image data. The present invention further relates to a method of preparing a data set including image-relating information and an image data, and still further to a computer readable medium on which is stored a program module for preparing a data set including image-relating information and an image data.

2. Discussion of the Background

Various types of imaging apparatus which generates, creates, produces, or the like (hereinafter referred to as generates) are used for various purposes. For example, medical images are generated in a medical imaging apparatus such as, for example, an X-ray diagnosis apparatus, an X-ray computed tomography apparatus (hereinafter referred to as a CT apparatus), a magnetic resonance imaging apparatus (hereinafter referred to as an MRI apparatus), a nuclear medicine diagnosis apparatus, an ultrasound diagnosis apparatus, or an endoscope. The generated medical images may be used for diagnosis, therapy, treatment, finding of affected part (or tumor), or the like. The generated medical images may be transmitted to and stored in an image filing server.

Typically, image data for one or more medical images are accompanied by several kinds of information of a patient imaged and an imaging condition. Such accompanying information is usually referenced by a doctor who interprets, diagnoses, or observes the images as useful information.

When the image data and the accompanying information are transmitted through a network, stored in the image filing server, or the like as a data set, the accompanying information is often placed first and the image data may be follow the accompanying information. Consequently, in order to display the one or more images, a display apparatus usually accesses and analyzes the accompanying information first and then finds the image data after the completion of the analysis. This delays the image display. In other words, it takes time to accomplish an actual display of the images after the doctor has operated to instruct the image display. This delay may annoy the doctor.

This problem may also apply to a well-known format called DICOM (digital imaging and communication in medicine) format. Although Japanese Application Publication No. P2002-41550 describes an easier display technique of a DICOM format data set, this technique requires additional processing and still causes delay in an original image display.

SUMMARY OF THE INVENTION

According to the first aspect of the present invention, there is provided an image storing apparatus for storing at least one image based on an image data generated by an imaging apparatus. The image storing apparatus includes a receiving unit, a processor, and a storage device. The receiving unit is configured to receive the image data. The processor is configured to prepare image-relating information and prepare a data set including the image-relating information and the image data following the image-relating information. The processor prepares leading information leading to the image data as part of the image-relating information. The storage device is configured to store the data set.

According to the second aspect of the present invention, there is provided an image display apparatus for displaying at least one image based on an image data generated by an imaging apparatus. The apparatus includes a receiving unit, a processor, and a display. The receiving unit is configured to receive the image data. The processor is configured to prepare image-relating information and prepare a data set including the image-relating information and the image data following the image-relating information. The processor prepares leading information leading to the image data as part of the image-relating information. The display is configured to display the at least one image in accordance with the leading information and the image data.

According to the third aspect of the present invention, there is provided an imaging apparatus for generating an image data for at least one image. The apparatus includes an image generating unit and a processor. The image generating unit is configured to generate the image data. The processor is configured to prepare image-relating information and prepare a data set including the image-relating information and the image data following the image-relating information. The processor prepares leading information leading to the image data as part of the image-relating information.

According to the fourth aspect of the present invention, there is provided an information processing apparatus. The apparatus includes a receiving unit, a processor, and an output unit. The receiving unit is configured to receive an image data for at least one image. The processor is configured to prepare image-relating information and prepare a data set including the image-relating information and the image data following the image-relating information. The processor prepares leading information leading to the image data as part of the image-relating information. The output unit is configured to output the data set.

According to the fifth aspect of the present invention, there is provided a method of preparing a data set. The method begins by preparing leading information which leads to an image data for at least one image. The image data is included in the data set. The method continues by preparing image-relating information including the leading information, preparing the data set including the image-relating information and the image data following the image-relating information.

According to the sixth aspect of the present invention, there is provided a method of preparing a data set. The method begins by calculating a size of at least part of image-relating information to be included in the data set and determining leading information leading to an image data to be included in the data set based on the calculated size. The method continues by incorporating the determined leading information into the image-relating information and preparing the data set including the image-relating information and the image data following the image-relating information.

According to the seventh aspect of the present invention, there is provided a method of preparing a data set for a plurality of images. The method begins by calculating a first size of a first part of image-relating information to be included in the data set, determining direct leading information leading to one or more of the plurality of images based on the calculated first size, and preparing multiframe information to be included in the image-relating information. The direct leading information is incorporated into the multiframe information. The method continues by calculating a second size of a second part of the image-relating information and determining indirect leading information leading to the multiframe information based on the calculated second size. The method further continues by incorporating the indirect leading information and the multiframe information into the image-relating information and preparing the data set including the image-relating information and an image data for the plurality of images following the image-relating information.

According to the eighth aspect of the present invention, there is provided a computer readable medium on which is stored a program module for preparing a data set. The program module has instructions, which when executed perform steps including preparing leading information which leads to an image data for at least one image. The image data is included in the data set. The steps also include preparing image-relating information including the leading information and preparing the data set including the image-relating information and the image data following the image-relating information.

According to the ninth aspect of the present invention, there is provided a computer readable medium on which is stored a program module for preparing a data set. The program module has instructions, which when executed perform steps including calculating a size of at least part of image-relating information to be included in the data set and determining leading information leading to an image data to be included in the data set based on the calculated size. The steps also include incorporating the determined leading information into the image-relating information and preparing the data set including the image-relating information and the image data following the image-relating information.

According to the tenth aspect of the present invention, there is provided a computer readable medium on which is stored a program module for preparing a data set for a plurality of images. The program module has instructions, which when executed perform steps including calculating a first size of a first part of image-relating information to be included in the data set, determining direct leading information leading to one or more of the plurality of images based on the calculated first size, and preparing multiframe information to be included in the image-relating information. The direct leading information is incorporated into the multiframe information. The steps also include calculating a second size of a second part of the image-relating information and determining indirect leading information leading to the multiframe information based on the calculated second size. The steps further include incorporating the indirect leading information and the multiframe information into the image-relating information and preparing the data set including the image-relating information and an image data for the plurality of images following the image-relating information.

BRIEF DESCRIPTION OF THE DRAWINGS

A more complete appreciation of embodiments of the present invention and many of its attendant advantages will be readily obtained by reference to the following detailed description considered in connection with the accompanying drawings, in which.

DESCRIPTION OF THE PREFERRED EMBODIMENTS

Embodiments of the present invention will be described with reference to the accompanying drawings. Recently a lot of computers have been used for various purposes. People use computers, for example, to transmit and/or receive various types of information through a network such as, for example, the Internet or a local area network (LAN). The received information may be stored in the computers or a storage apparatus which may be called a server. The information may include image data. The computer may be incorporated in various apparatuses. In addition, the computer may have a feature of copying and storing as image data a screen image which is currently displayed in a screen of the computer whether the displayed image is obtained as a result of the network communication or not.

Figure 1:
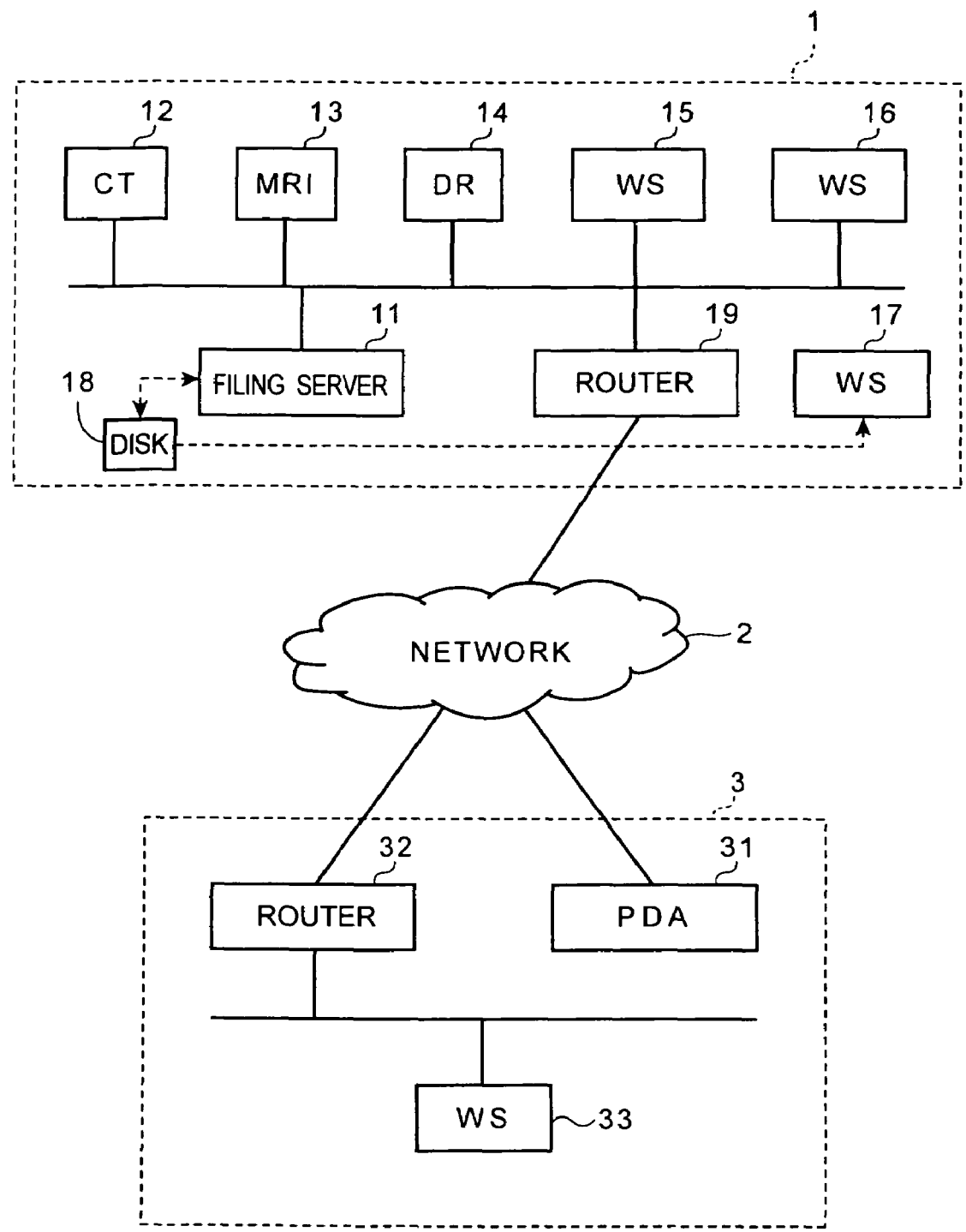
FIG. 1 is an illustration showing an example of a picture archiving and communication system (PACS)

Such network communication also improves a social infrastructure and makes things easier or more convenient in a lot of social fields One example is an application to a medical field. FIG. 1 is an illustration showing an example of a picture archiving and communication system (PACS) which has become popular recently in medical facilities.

The PACS shown in FIG. 1 includes a hospital 1, a network 2, and an external facility 3 other than the hospital 1. The external facility 3 may be a medical facility such as, for example, another hospital, a clinic, or a medical practitioner's office, or may be a doctor's house. When the doctor brings a portable computer, the external facility 3 includes the doctor himself/herself.

The hospital 1 includes a filing server 11, a CT apparatus 12, an MRI apparatus 13, a digital radiography apparatus (hereinafter referred to as a DR apparatus) 14, workstations 15, 16, and 17, a memory disk 18, and a router 19. The filing server 11, the CT apparatus 12, the MRI apparatus 13, the DR apparatus 14, the workstations 15 and 16, and the router 19 may be coupled to one another through a hospital LAN.

The filing server 11 is an example of an image storing apparatus and may be accomplished by a computer. The filing server 11 may include a receiving unit, a processor, a storage device, an output unit, a memory driver, and a controller. The storage device includes one or more large capacity memory disks which are capable of storing various types of information including image data. The receiving unit typically receives image data and/or image-relating information from the CT apparatus 12, the MRI apparatus 13, and the DR apparatus 14 through the hospital LAN. The output unit also usually outputs (or transmits) image data and/or image-relating information stored in the large capacity memory disks through the hospital LAN upon requests or according to a predetermined instruction. The memory driver such as, for example, a disk driver reads information from the memory disk 18. The memory driver may read image data and/or image-relating information stored in the memory disk 18. In addition, the memory driver may also be used to write information to the memory disk 18. The information may include image data and/or image-relating information stored in the filing server 11.

The CT apparatus 12, the MRI apparatus 13, and the DR apparatus 14 are imaging apparatuses and generate CT image data, MRI image data, and DR image data by their image generating units, respectively. Imaging apparatuses are not limited to these apparatuses, but may, in addition or alternatively, be, for example, an X-ray diagnosis apparatus, a nuclear medicine diagnosis apparatus, an ultrasound diagnosis apparatus, and/or an endoscope. The generated image data and its relating information (the image-relating information) are typically transmitted to the filing server 11. The generated image data and the image-relating information may also be transmitted to the workstation(s) 15 and/or 16 upon requests or according to a predetermined instruction. The generated image data and the image-relating information may alternatively be stored in the memory disk 18 so as to be read in the filing server 11 or the workstation 15, 16, or 17.

The workstations 15 to 17 are examples of an image display apparatus and may be called viewers. The workstations 15 to 17 may be provided, for example, in an image interpretation room or in a consultation room. In FIG. 1, the workstation 17 is not connected to the hospital LAN but may be capable of reading the image data and/or the image-relating information stored in the memory disk 18. The workstations 15 and 16 may be capable of reading the image data and/or the image-relating information stored in the memory disk 18, as similar to the workstation 17. The workstations 15 and 16 may receive the image data and the image-relating information from the filing server 11, the CT apparatus 12, the MRI apparatus 13, and/or the DR apparatus 14 as a regular operation by their receiving units. In addition or alternatively, the workstations 15 and 16 may request a data transmission to the filing server 11, the CT apparatus 12, the MRI apparatus 13, or the DR apparatus 14 and receive the image data and/or the image-relating information through the hospital LAN by the receiving units. The workstations 15 to 17 can display the image data and/or the image-relating information received through the hospital LAN or the memory disk 18 in their displays. The workstations 15 to 17 may be used by doctors or nurses (hereinafter referred to as doctors).

The memory disk 18 may be a portable (or detachable) memory disk such as, for example, a CD-ROM, a DVD-ROM, a magnetic disk, a magnetic-optical disk, an optical disk, a semiconductor memory, or the like. The memory disk 18 may be used to store the image data and/or the image-relating information.

The router 19 is used, for example, when the filing server 11 communicates with an apparatus in the external facility 3 through the network 2. The router 19 may be operated as a gateway or a firewall for securing information obtained in the hospital 1. The router 19 may also be operative as an information processing apparatus described below.

The network 2 may be a public telephone network, a private network, the Internet, or the like. The network 2 may also be a wired network such as, but not limited to, an optical network or an electrical network, or a wireless network.

The external facility 3 includes a personal digital assistance (or a personal digital assistant) (PDA) 31, a router 32, and a workstation 33. The PDA 31 is an example of an image display apparatus and may work as a portable viewer. When the PDA 31 is used in a wireless communication manner, the PDA 31 can be directly connected to its base station via a radio link in the network 2. The doctor can bring the PDA 31 with him/her as the portable computer and can receive by its receiving unit and observe in its display the image data and/or the image-relating information nearly wherever he/she is although it may not be possible for the doctor to have image data whose resolution is high enough to interpret.

The router 32 is used, for example, when the workstation 33 or the PDA 31 communicates with the filing server 11 through the network 2. The router 32 may be operated as a gateway or a firewall for securing information obtained in the external facility 3. The router 32 may also be operative as an information processing apparatus described below.

The workstation 33 is an example of an image display apparatus and may be called a viewer. The workstation 33 may receive by its receiving unit the image data and the image-relating information from the filing server 11, the CT apparatus 12, the MRI apparatus 13, and/or the DR apparatus 14 as a regular operation through the hospital LAN, the router 19, the network 2, and the router 32. In addition or alternatively, the workstation 33 may request a data transmission to the filing server 11, the CT apparatus 12, the MRI apparatus 13, or the DR apparatus 14 and receive the image data and/or the image-relating information through the router 32, the network 2, the router 19, and the hospital LAN. When the workstation 33 is capable of reading information stored in the memory disk 18, the workstation 33 may read the image data and/or the image-relating information stored in the memory disk 18. The workstation 33 can display the image data and/or the image-relating information received through the network 2 or the memory disk 18 in its display. The workstation 33 may be used by the doctors.

The above-mentioned image data may include data for only one image and, if necessary, its incidental information (hereinafter referred to as image data for one image) or data for a plurality of images, a series of images, or multiframe images and, if necessary, their respective incidental information (hereinafter referred to as image data for a plurality of images). Multiframe information which may be necessary when the image data is for a plurality of images may, however, be included in the image-relating information.

The above-mentioned image-relating information may include information of a patient who was imaged by the CT apparatus 12, the MRI apparatus 13, or the DR apparatus 14. The information of the patient may include, for example, one or more of a patient name, a patient identification information (hereinafter referred to as a patient ID), and a patient age. The image-relating information may also include information of an examination in which the image data was acquired with respect to the patient. The information of the examination may include, for example, one or more of an examination date, a type (or a kind) of the imaging apparatus, and an examination condition.

In order to reduce time to access and obtain one or more images to transmit, to write to the memory disk 18, or to display, the image-relating information includes leading information which may be prepared and formed in a manner as described below. A flowchart shown in FIG. 2 and data formats in the drawings are only examples and any other similar, modified, alternative, or possible flow and data format can be applied for the same purpose within a scope of the present invention. One or more image-relating information preparation software programs may be installed in the filing server 11, the CT apparatus 12, the MRI apparatus 13, the DR apparatus 14, the workstations 15, 16, 17, 33, the PDA 31, the routers 19, and/or 32 so that the above software-installed apparatus or the like can prepare the image-relating information and makes it possible to execute, for example, the image display in a time-reduced manner, in accordance with flowcharts shown in the drawings. A specific information processing apparatus incorporating the software programs may also be provided in the PACS shown in FIG. 1 so as to prepare the image-relating information. The information processing unit may be coupled to the CT apparatus 12, the MRI apparatus 13, and/or the DR apparatus 14. The information processing unit may also be coupled to the filing server 11 or the workstations 15, 16, 33, and/or the PDA 31. The information processing apparatus may include a receiving unit which receives the image data and an output unit which outputs the image-relating information or a set of the image-relating information and the image data. Further, the software programs may be stored in a computer readable medium. The software programs may alternatively be provided to one or more of the above-mentioned apparatuses and the like for the installation through the LAN, the network 2, or another network.

Figure 2:
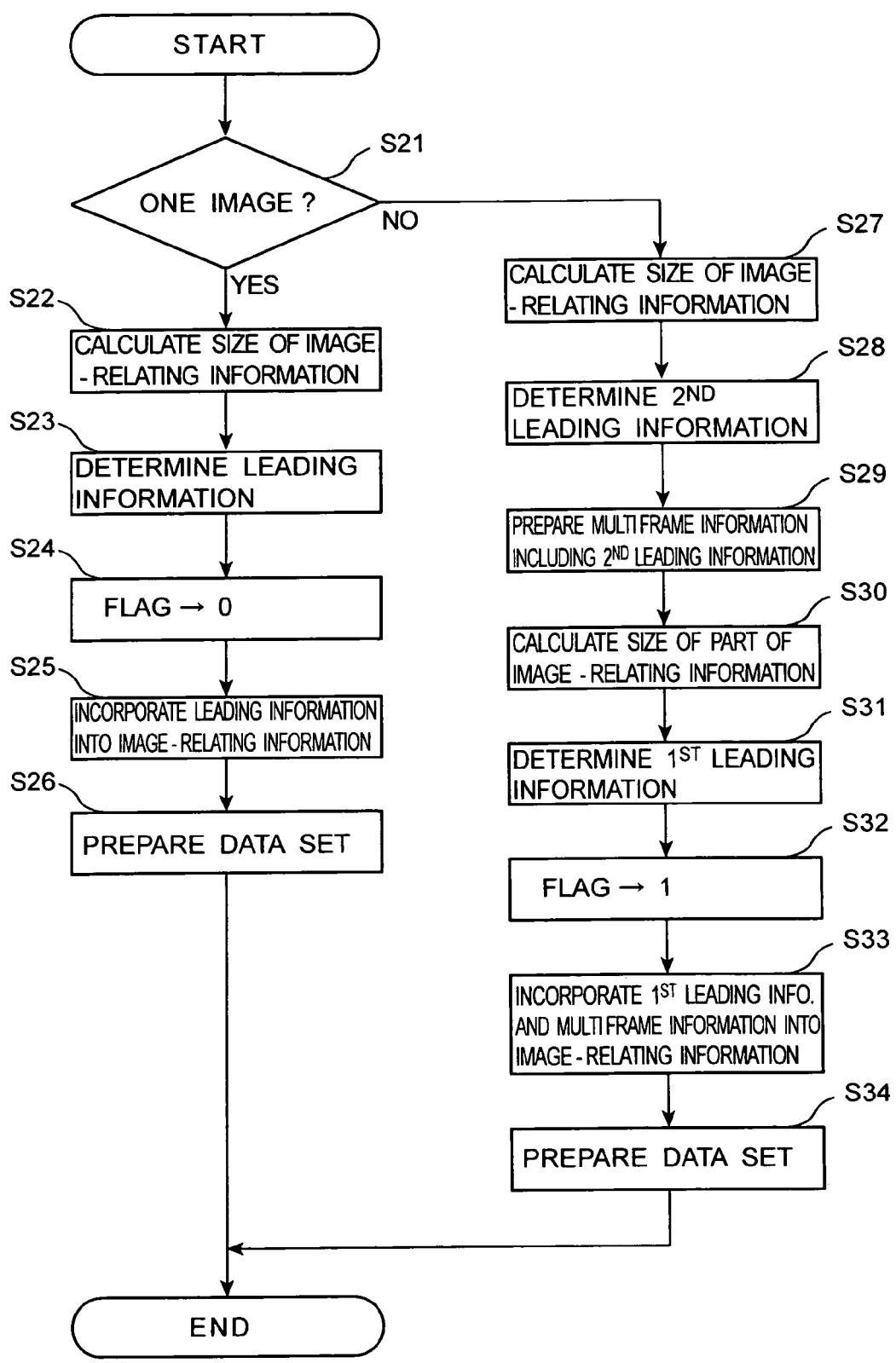
FIG. 2 is a flowchart showing an exemplary flow of preparing a data set including image-relating information and image data.

FIG. 2 is a flowchart showing an exemplary flow of preparing a data set including the image-relating information and the image data. The flow shown in FIG. 2 may be executed by a processor provided in the apparatus or the like shown in FIG. 1. The processor may be provided independently or be included in a controller provided in the apparatus or the like shown in FIG. 1. Whether the processor is provided in the controller or not, the processor and the controller are collectively hereinafter referred to as the controller. In FIG. 2, a flow with respect to a conventional technique of preparing image-relating information is omitted. A feature of the flowchart shown in FIG. 2 is a preparation and incorporation of leading information.

As a result of generation, reception, or other ways, when the controller recognizes the number of images included in the image data to be accompanied by the image-relating information, the controller determines whether the image data is for only one image or not (step S21). If there is only one image, the controller calculates a size of the image-relating information (step S22). As mentioned above, the image-relating information may include predetermined information of the patient and the examination and be basically prepared in a conventional manner. In the preparation, however, the image-relating information is to include leading information which will be described below. A data size of the leading information can be predetermined, and accordingly the size of the image-relating information can be calculated, considering the data size of the leading information.

The controller determines the leading information based on the calculation result in step S22 (step S23) The leading information may be defined to represent a position of the image data in the data set which also includes the image-relating information. In other words, the leading information may be a head address of the image data. The leading information may alternatively be a size or amount of data to the image data from a predetermined address, a head of the image-relating information, or predetermined information included in the image-relating information. The position of the image data represented by the leading information may not always be a head position of the image data but alternatively, for example, a position near to or around the head position.

The leading information may also include flag information. The flag information is an example of first identification information indicating whether the image data is for only one image or a plurality of images. When the image data is for only one image, the flag information is set to zero ('0') (step S24). The flag information is placed ahead of information of the position of the image data, but may alternatively be placed behind the information of the position of the image data.

The leading information is incorporated into a predetermined position of the image-relating information (step S25). The leading information may be assigned, provided, placed, or the like (hereinafter referred to as placed) at a head of the image-relating information. The preparation of the image-relating information has been completed by this incorporation. The controller finally combines the image-relating information and the image data so as to prepare the data set (step S26).

In step S21, if there are a plurality of images as the image data, the controller calculates a size of the image-relating information in a similar manner to step S22 (step S27). When the image data is for a plurality of images as in this case, a group of image data corresponding to each of a plurality of images may also be referred to as a plurality of images in the following description. The image-relating information may include predetermined information of the patient and the examination and be basically prepared in a conventional manner. In the preparation, however, the image-relating information is to include the first leading information (or indirect leading information) and multiframe information which will be described below. A data size of the first leading information and a data size of the multiframe information can be predetermined, and accordingly the size of the image-relating information can be calculated, considering the data size of the first leading information and the multiframe information.

The controller determines the second leading information (or direct leading information) based on the calculation result in step S27 (step S28). The second leading information may be defined to represent positions of the plurality of images in the data set. In other words, the second leading information may include a head address of each of the plurality of images. The second leading information may alternatively include a size or amount of data to each of the plurality of images from predetermined information included in the image-relating information, predetermined information included in the multiframe information, a predetermined address, a head of the image-relating information, or the beginning of the multiframe information. Each position of the plurality of images represented by the second leading information may not always be a head position of each of the plurality of images but alternatively, for example, a position near to or around the head position.

The controller then prepares the multiframe information (step S29). The multiframe information may basically be prepared in a conventional manner. In the preparation, however, the multiframe information includes the second leading information.

The controller then calculates a size of part of the image-relating information (step S30). The controller determines the first leading information based on the calculation result in step S30 (step S31). The first leading information may be defined to represent a position of the multiframe information in the data set. In other words, the first leading information may include a head address of the multiframe information. The first leading information may alternatively include a size or amount of data to the multiframe information from predetermined information included in the image-relating information, a predetermined address, or a head of the image-relating information. The position of the multiframe information represented by the first leading information may not always be a head position of the multiframe information but alternatively, for example, a position near to or around the head position.

The first leading information may also include flag information indicating whether the image data is for only one image or a plurality of images. When the image data is for a plurality of images, the flag information is set to one ('1') (step S32). The flag information is placed ahead of information of the position of the multiframe information, but may alternatively be placed behind the information of the position of the multiframe information.

The first leading information and the multiframe information are incorporated into predetermined positions of the image-relating information (step S33) The first leading information may be placed at a head of the image-relating information. The multiframe information may be placed at its typical or conventional position or an allowable position in the image-relating information. For example, the multiframe information may be placed at the end of the image-relating information. The preparation of the image-relating information has been completed by this incorporation. The controller finally combines the image-relating information and the image data (the plurality of images) so as to prepare the data set (step S34).

Figure 3A:
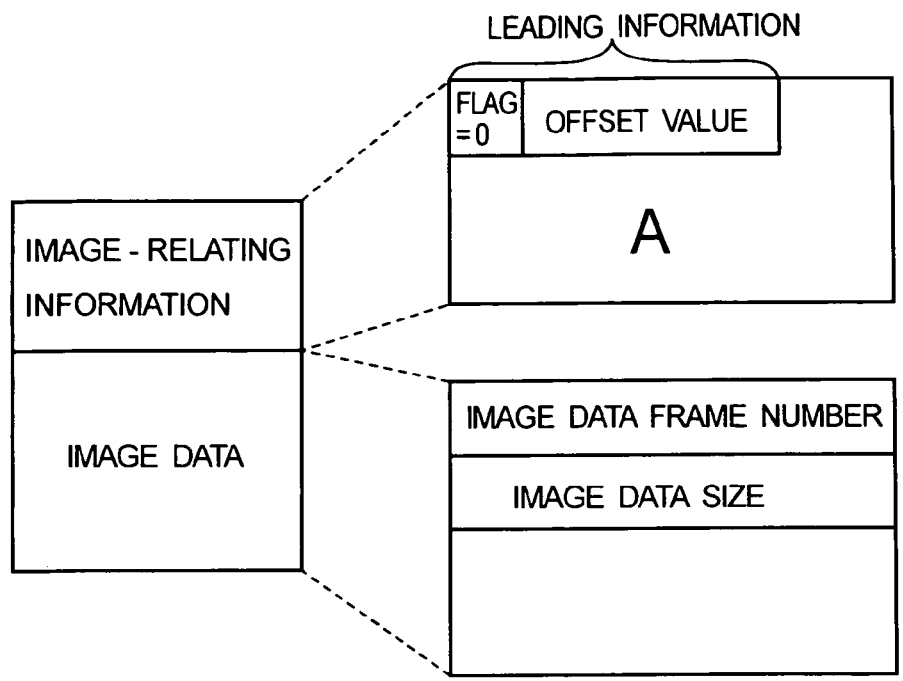
FIG. 3A is an illustration showing an example of a data format of the image-relating information when the image data is for only one image.

FIG. 3A is an illustration showing an example of a data format of the image-relating information when the image data is for only one image. As shown in FIG. 3A, the data set includes the image-relating information and the image data. Typically, the image data follows the image-relating information.

The image-relating information includes the leading information at a head of the image-relating information. The leading information includes the flag information and an offset value as information representing the position of the image data. The offset value may represent an offset amount from a head position of the data set to a head position of the image data. Since the flag information shows zero, the offset value leads directly to the head position of the image data in this example. The image data typically include information of an image data frame number and an image size.

Therefore, the controller can access the image data immediately after the analysis of the leading information without analyzing the rest A of the image-relating information. This direct access may be helpful to reduce time to display the one image or to transmit the one image through the hospital LAN or the network 2 or to write the one image to the memory disk 18.

Figure 3B:
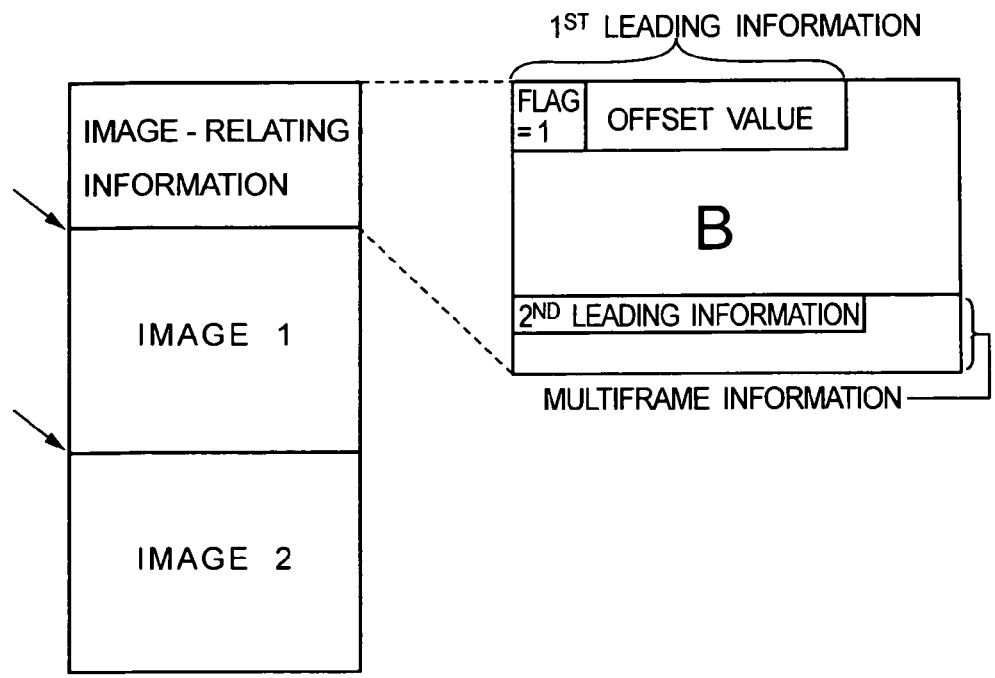
FIG. 3B is an illustration showing an example of a data format of the image-relating information when the image data is for a plurality of images.

FIG. 3B is an illustration showing an example of a data format of the image-relating information when the image data is for a plurality of images. As shown in FIG. 3B, the data set includes the image-relating information and the image data (image 1 and image 2). Typically, the image data follows the image-relating information.

The image-relating information includes the first leading information at a head of the image-relating information. The image-relating information also includes the multiframe information. The first leading information includes the flag information and an offset value as information representing the position of the multiframe information. The offset value may represent an offset amount from a head position of the data set to a head position of the multiframe information. Since the flag information shows one, the offset value leads to the head position of the multiframe information in this example. The multiframe information includes the second leading information. The second leading information leads to a head of the image 1 and a head of the image 2.

Therefore, the controller can access the multiframe information immediately after the analysis of the first leading information without analyzing other image-relating information B between the first leading information and the multiframe information. Since the access to the image data is indirect via the multiframe information, the access speed may be inferior to that in the format shown in FIG. 3A. Compared to the conventional access speed to a plurality of images, however, this access may be helpful to reduce time to display the plurality of images or to transmit the plurality of images through the hospital LAN or the network 2 or to write the plurality of images to the memory disk 18.

In addition, when the multiframe information is placed at the end of the image-relating information, it may be possible to avoid affecting other information of the image-relating information even if the number of images increases and accordingly the size of the multiframe information increases.

Figure 4A:
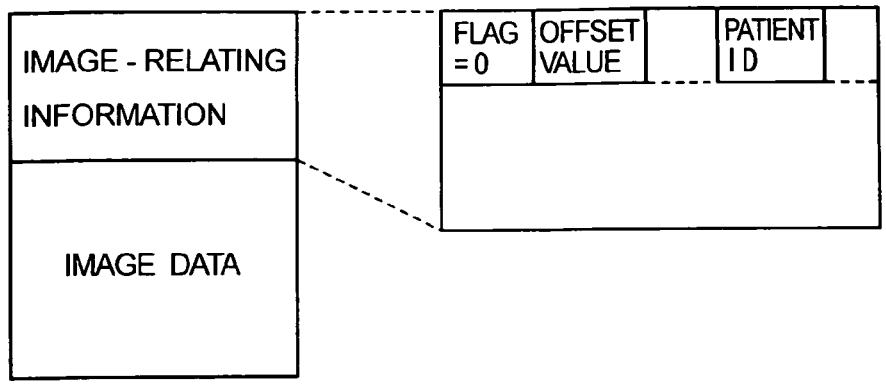
FIGS. 4A to 4C are illustrations showing another examples of data formats of the image-relating information.
Figure 4B:
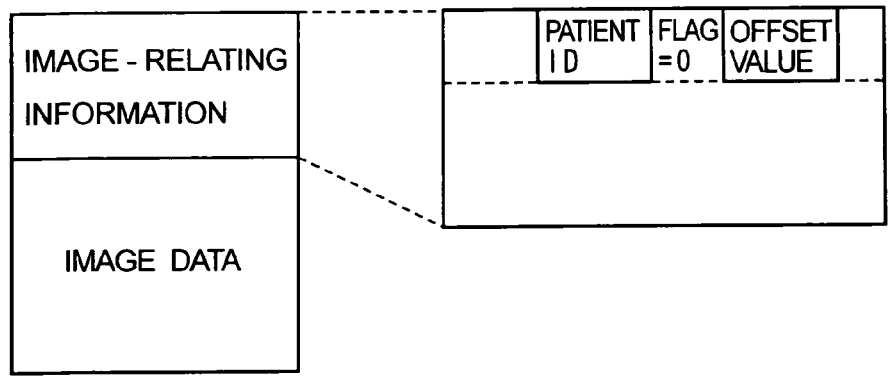
Figure 4C:
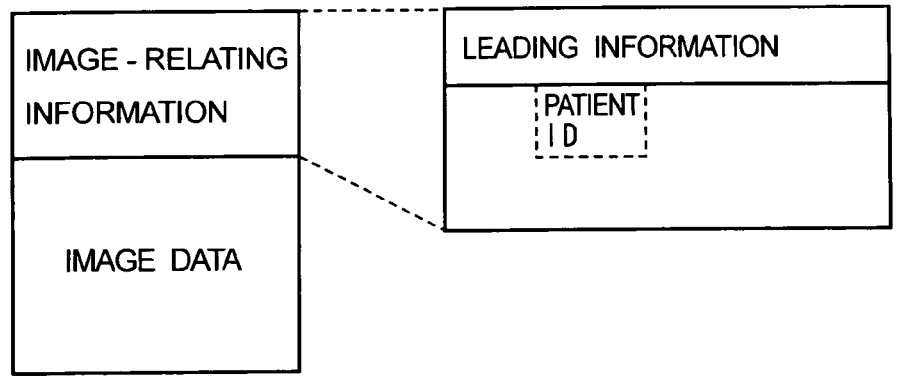

The leading information or the first leading information can be placed at various positions other than the head of the image-relating information. FIGS. 4A to 4C are illustrations showing various examples of a data format of the image-relating information. As shown in FIG. 4A, the image-relating information includes the (first) leading information comprising the flag information and the offset value at a head of the image-relating information. Immediately after or some information after the (first) leading information, there is included patient ID in the image-relating information. In this case, the controller may continue to analyze the image-relating information until the patient ID is analyzed so that the controller can verify that the patient ID is agreed or identical with a patient ID for targeted image data. After the verification, the controller may access the image data following the image-relating information or the multiframe information.

As shown in FIG. 4B, the image-relating information includes the (first) leading information comprising the flag information and the offset value. Immediately before or some information before the (first) leading information, there is included patient ID in the image-relating information. In this case, the controller may continue to analyze the image-relating information after the patient ID has been analyzed and verified. After the analysis of the (first) leading information, the controller may access the image data following the image-relating information or the multiframe information.

The (first) leading information may alternatively be provided within a predetermined field of the image-relating information. The predetermined field may be placed at a head of the image-relating information as shown in FIG. 4C. After the analysis of the (first) leading information, the controller may access the image data following the image-relating information or the multiframe information. The controller may do the same after the verification of the patient ID information.

Figure 5:
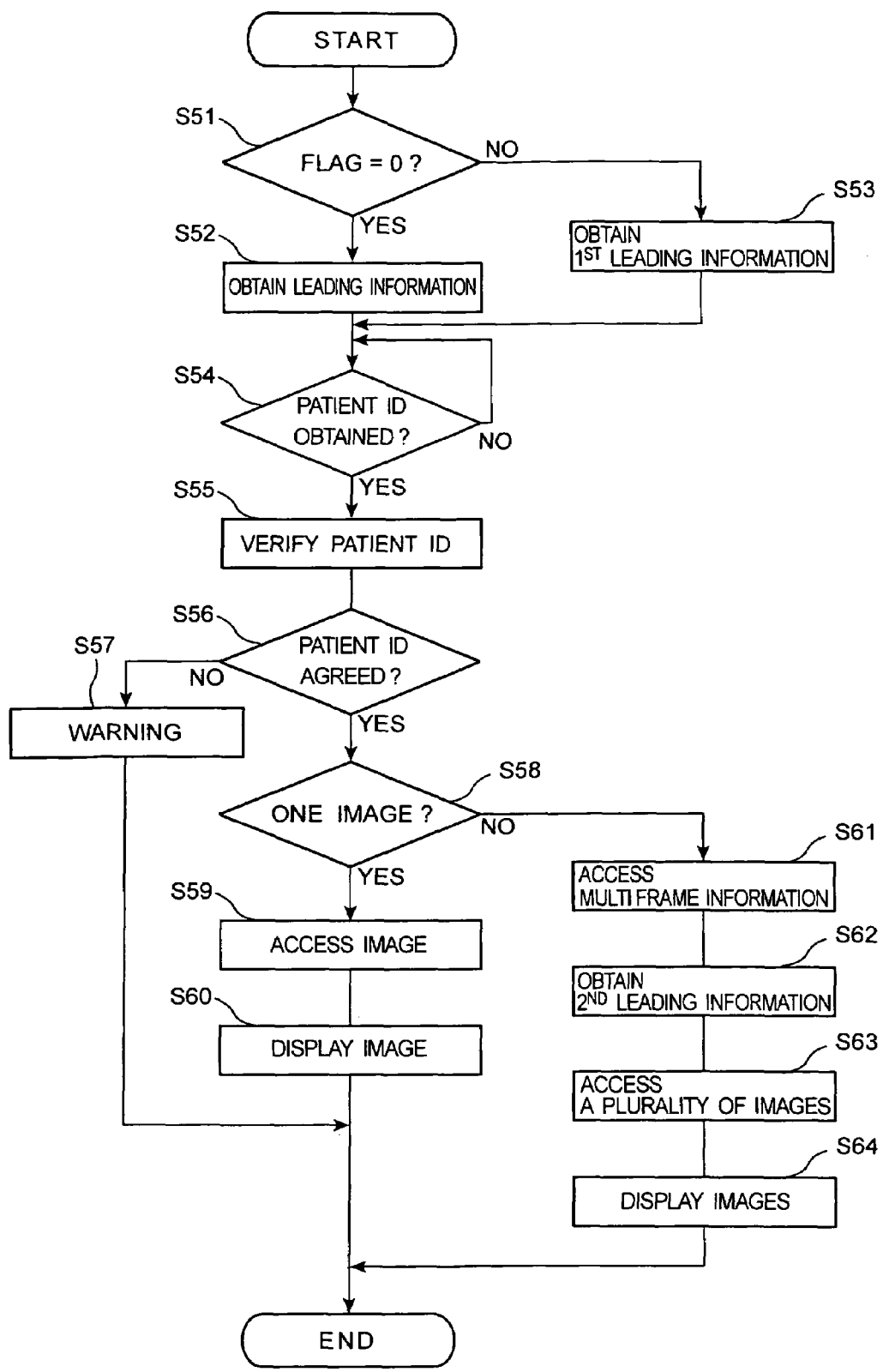
FIG. 5 is a flowchart showing an exemplary flow of an operation of displaying image(s) according to the data format shown in FIG. 4A.

FIG. 5 is a flowchart showing an exemplary flow of an operation of displaying the one image or the plurality of images according to the data format shown in FIG. 4A.

The controller accesses the image-relating information, for example, when an image display has been requested. When the controller accesses the flag information, the controller determines whether the flag information indicates zero or not (step S51). When the flag information indicates zero, the controller accesses and obtains the leading information leading to the image data (one image) (step S52). If the flag information indicates one, the controller accesses and obtains the first leading information leading to the multiframe information (step S53).

The controller continues to analyze the image-relating information and accesses patient ID (step S54). The controller obtains the patient ID and verifies the patient ID based on patient ID information included in an image display request (step S55). If the patient ID obtained from the image-relating information and the patient ID information included in the image display request are not agreed (step S56), the controller controls to warn the doctor by displaying a warning message, beeping, or the like (step S57).

When the patient ID is agreed in step S58, the controller determines whether the image data is for only one image or not (step S58). This is determined based on the flag information accessed in step S51. When the image data is for only one image or the flag information indicates zero, the controller accesses the image data (one image) in accordance with the leading information (step S59). The accessed one image is displayed in the same apparatus or in another apparatus after the accessed image data has been transmitted to another apparatus (step S60).

When the image data is for a plurality of images or the flag information indicates one, the controller accesses the multiframe information in accordance with the first leading information (step S61). The controller then analyzes the multiframe information and obtains the second leading information included in the multiframe information (step S62). The controller accesses the image data (the plurality of images) in accordance with the second leading information (step S63) The accessed plurality of images are displayed in the same apparatus or in another apparatus after the accessed image data has been transmitted to another apparatus (step S64).

In steps S60 and S64, only the image data transmission may be made instead of the image(s) display.

In the above embodiment, the data format of the image-relating information has been different as shown in FIGS. 3A and 3B according to whether the image data is for only one image or a plurality of images. The data format may, however, be unified regardless of the number of images included in the image data. When the data format is common or similar regardless of the number of images, the leading information may not need the flag information to distinguish between the image data for only one image and a plurality of images, which may be advantageous of further reducing access time.

Figure 6A:
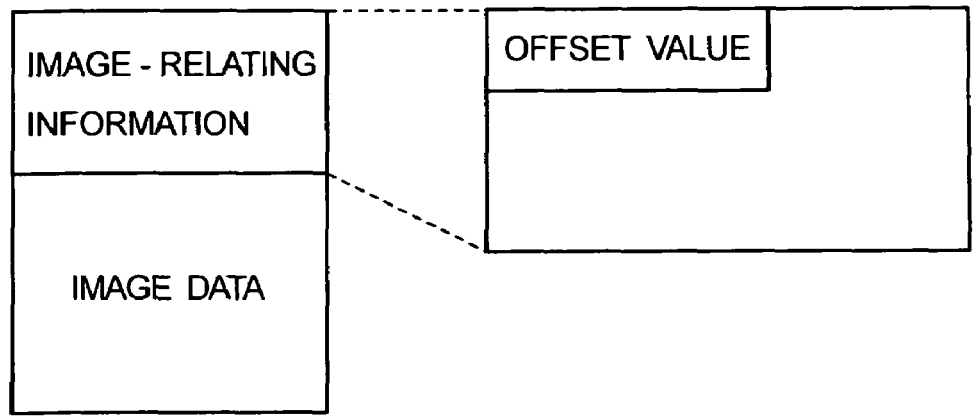
FIGS. 6A and 6B are illustrations showing an example of a data format which is common to the image-relating information for only one image and a plurality of images.
Figure 6B:
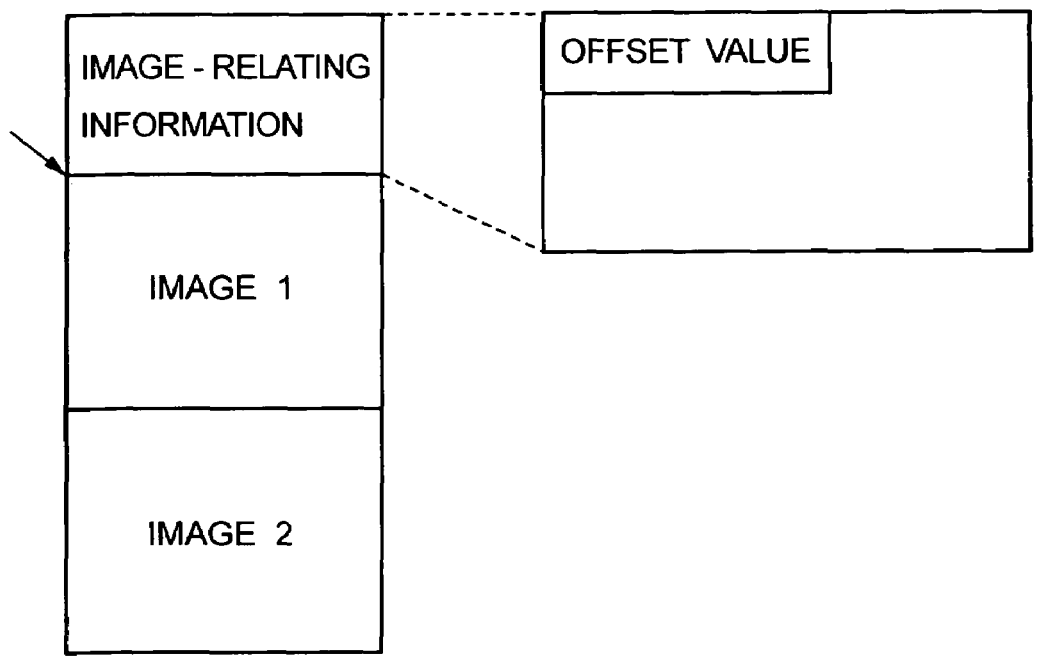

FIGS. 6A and 6B are illustrations showing an example of a data format which is common to the image-relating information for only one image and a plurality of images. As shown in FIG. 6A, the image-relating information accompanies the image data for only one image and includes an offset value as the leading information but not the flag information. In FIG. 6B, although the image-relating information accompanies the image data for a plurality of images, the image-relating information includes neither the flag information nor the multiframe information. The image-relating information includes an offset value. Since the image-relating information does not include the multiframe information, the leading information, which is not the first leading information, may lead to a head of the image data. The leading information may alternatively lead to a specific one of the plurality of images. In addition, the size of the offset value in FIG. 6B may be identical to that in FIG. 6A since the leading information does not lead to the plurality of images.

Figure 7:
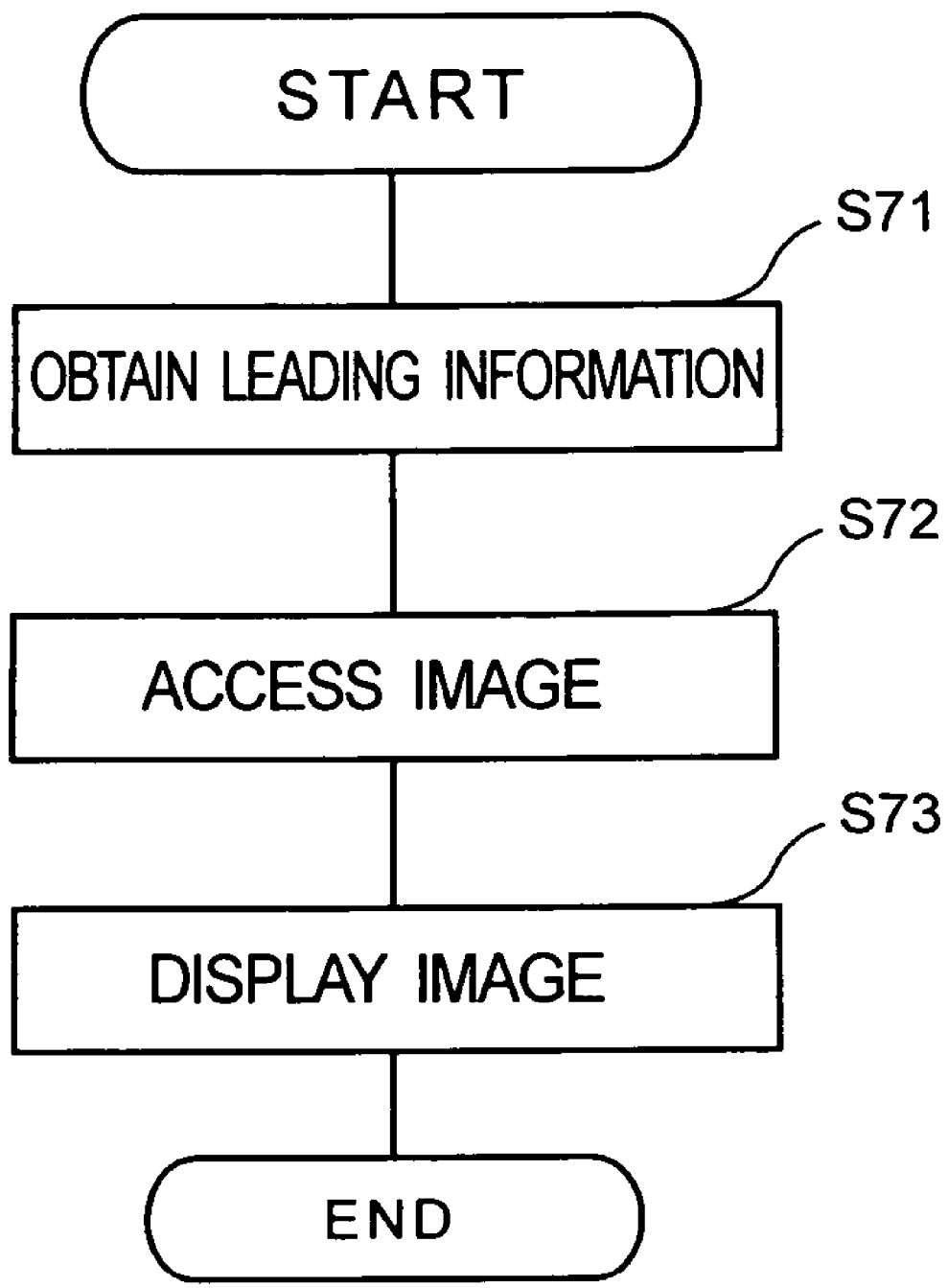
FIG. 7 is a flowchart showing an exemplary flow of an operation of displaying image(s) according to the data format shown in FIGS. 6A and 6B.

FIG. 7 is a flowchart showing an exemplary flow of an operation of displaying image(s) according to the data format shown in FIGS. 6A and 6B. Although FIG. 7 does not show that the controller verifies the patient ID, the controller may verify the patient ID as shown in FIG. 5.

The controller accesses the image-relating information, for example, when an image display has been requested. The controller accesses and obtains the leading information (step S71). Immediately after having obtained the leading information, the controller may access the image data in accordance with the leading information (step S72). If the image data is for only one image, the controller accesses the one image and the accessed one image is displayed in the same apparatus or in another apparatus after the accessed image data has been transmitted to another apparatus (step S73). If the image data is for a plurality of images, the controller may access the first image of the plurality of images and the accessed first image is displayed in the same apparatus or in another apparatus after the accessed image data has been transmitted to another apparatus. After the first image display, the subsequent images may be displayed in turn or in parallel. In step S73, only the image data transmission may be made instead of the image display.

Figure 8A:
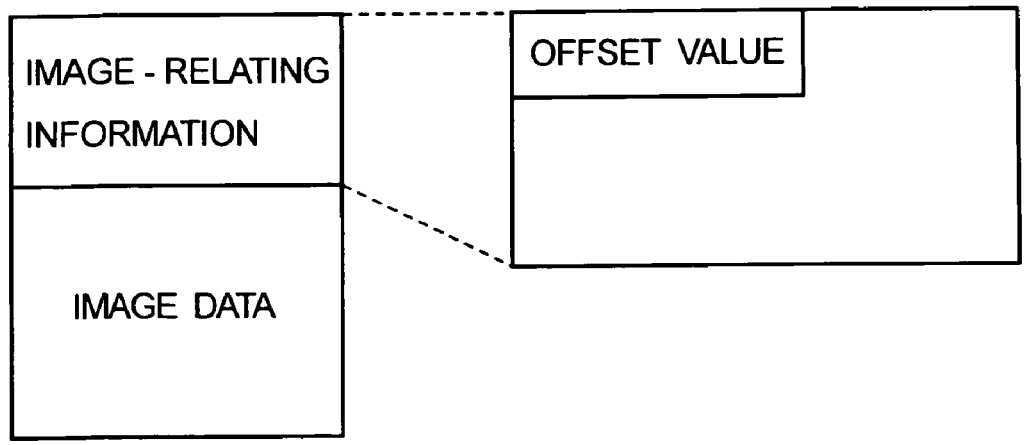
FIGS. 8A and 8B are illustrations showing a modified example of the data format shown in FIGS. 6A and 6B.
Figure 8B:
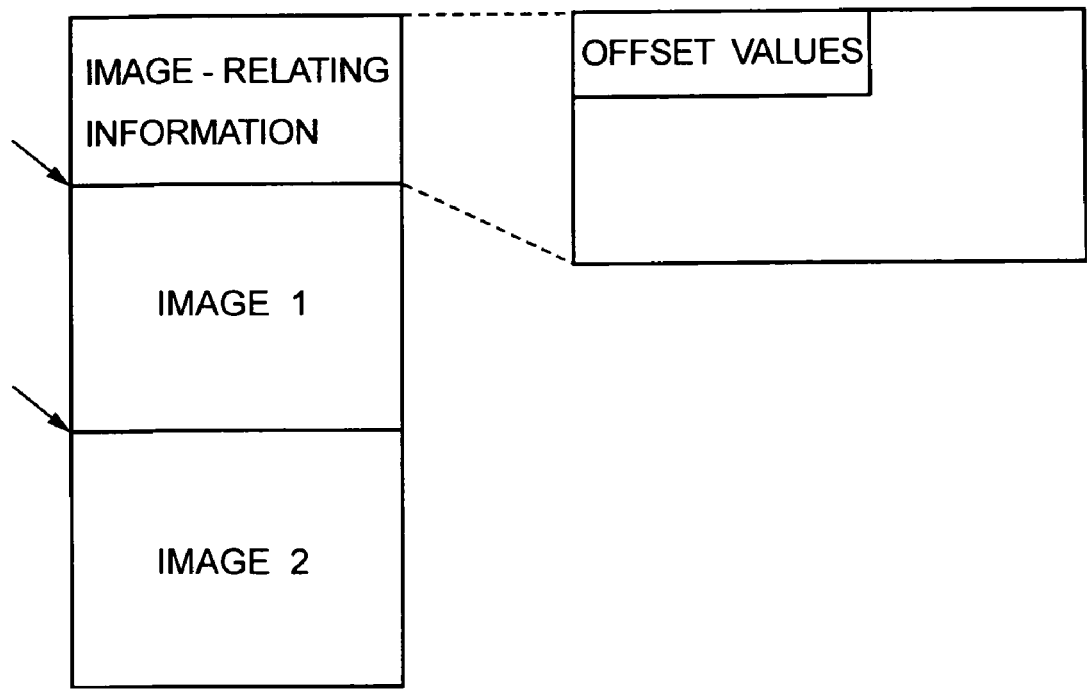

FIGS. 8A and 8B are illustrations showing a modified example of the data format shown in FIGS. 6A and 6B. FIG. 8A is the same as that shown in FIG. 6A. As shown in FIG. 8B, however, the image-relating information accompanies the image data for a plurality of images and includes offset values as the leading information which may lead to the plurality of images. The size of the offset values in FIG. 8B may be larger than that shown in FIG. 8A since the offset value shown in FIG. 8A leads to only one image. This data format may be applicable if the size of the offset values leading to the plurality of images is not too large to be included in the image-relating information or to be placed at a specific position in the image-relating information.

Figure 9:
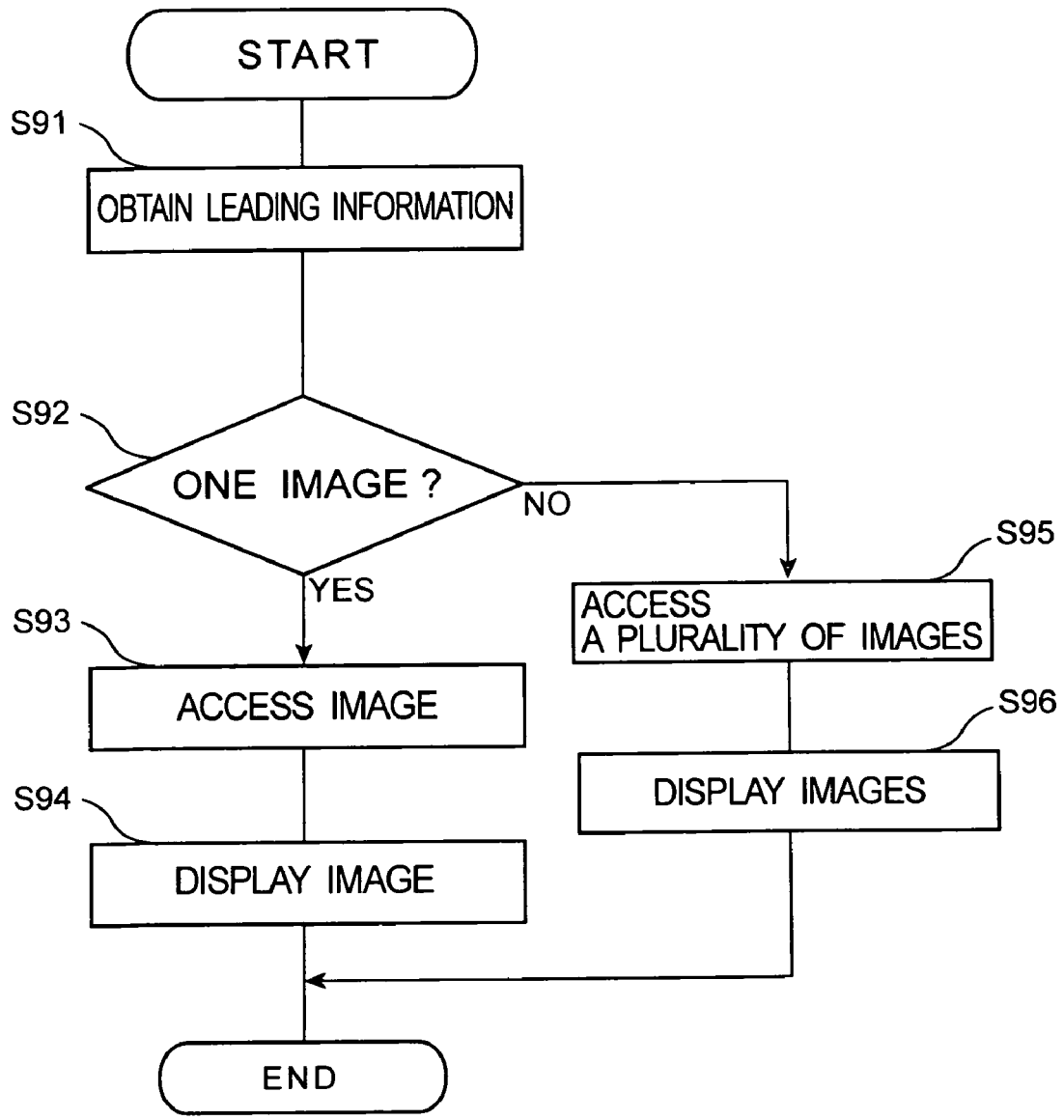
FIG. 9 is a flowchart showing an exemplary flow of an operation of displaying image(s) according to the data format shown in FIGS. 8A and 8B.

FIG. 9 is a flowchart showing an exemplary flow of an operation of displaying image(s) according to the data format shown in FIGS. 8A and 8B. Although FIG. 9 does not show that the controller verifies the patient ID information, the controller may verify the patient ID information as shown in FIG. 5.

The controller accesses the image-relating information, for example, when an image display has been requested. The controller accesses and obtains the leading information (step S91). The controller determines whether the leading information includes the offset value for only one image or not (step S92). When the image data is for only one image, the controller may access the image data (the one image) in accordance with the offset value (step S93). The accessed one image is displayed in the same apparatus or in another apparatus after the accessed image data has been transmitted to another apparatus (step S94). If the image data is for a plurality of images, the controller may access the image data (the plurality of images) in accordance with the offset values (step S95). The accessed plurality of images are displayed in the same apparatus or in another apparatus after the accessed image data has been transmitted to another apparatus (step S96). The plurality of images may be displayed in parallel. In steps S94 and S96, only the image data transmission may be made instead of the image(s) display.

Figure 10A:
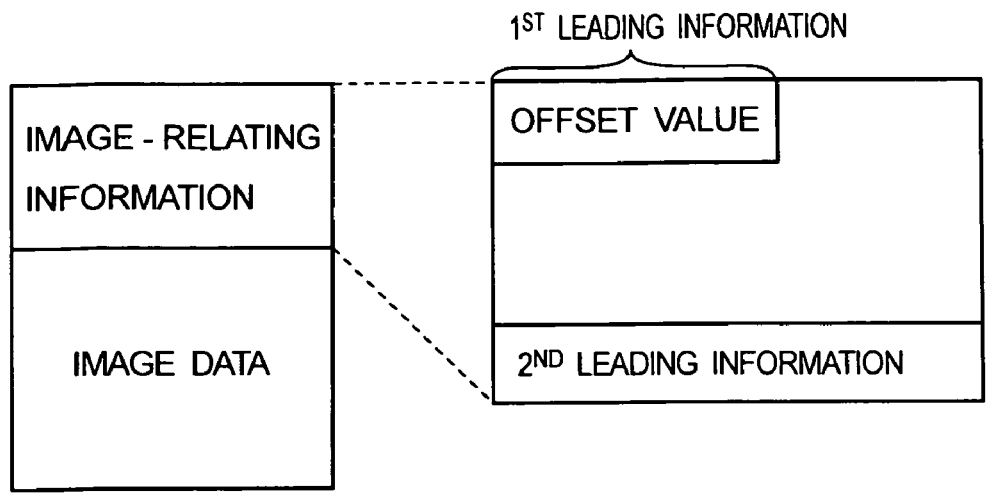
FIGS. 10A and 10B are illustrations showing another example of a data format which is common to the image-relating information for only one image and a plurality of images.
Figure 10B:
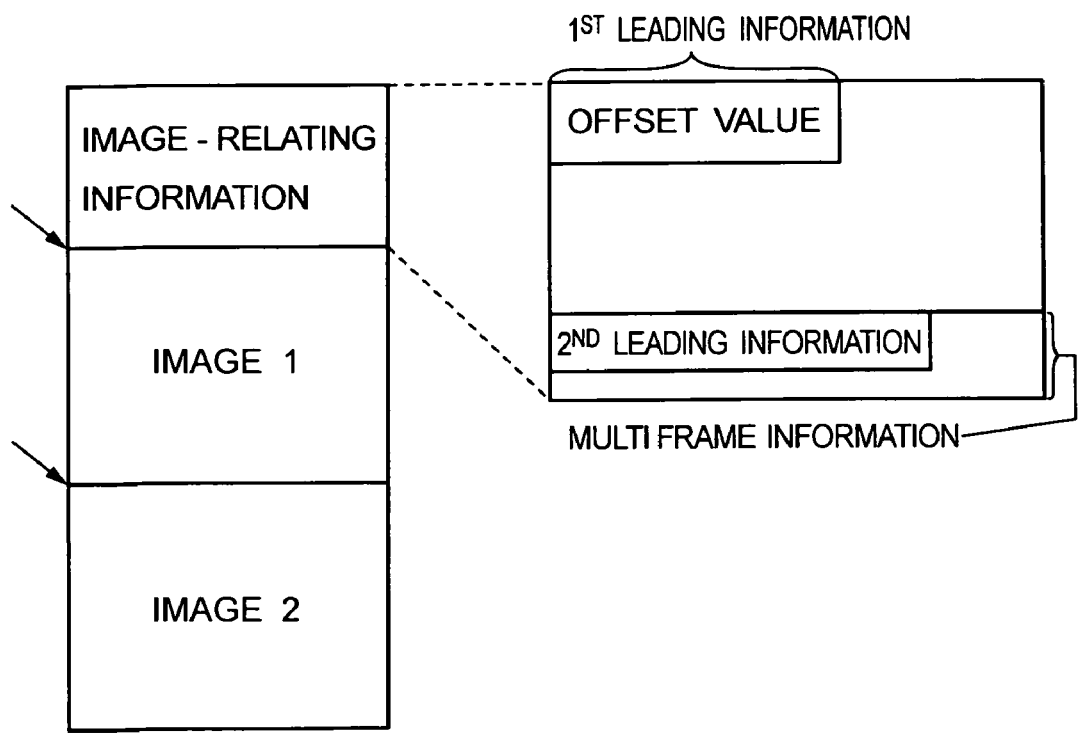

FIGS. 10A and 10B are illustrations showing another example of a data format which is common to the image-relating information for only one image and a plurality of images. As shown in FIG. 10A, the image-relating information accompanies the image data for only one image and includes an offset value as the first leading information but not the flag information. Although the image-relating information shown in FIG. 10A is for one image, the image-relating information also includes the second leading information which may correspond to multiframe information. The second leading information may lead to the one image. In FIG. 10B, the image-relating information accompanies the image data for a plurality of images and includes an offset value as the first leading information but not the flag information. Since the image-relating information shown in FIG. 10B is for a plurality of images, the image-relating information also includes multiframe information including the second leading information. The second leading information may lead to the plurality of images. In this example, the image-relating information shown in FIG. 10A becomes larger in size than that shown in FIGS. 6A and 8A. However, the controller does not need to analyze the flag information and can immediately access the leading information when image data is for only one image while the controller does not need to analyze the flag information and still can access the plurality of images in parallel when the image data is for the plurality of images.

Figure 11:
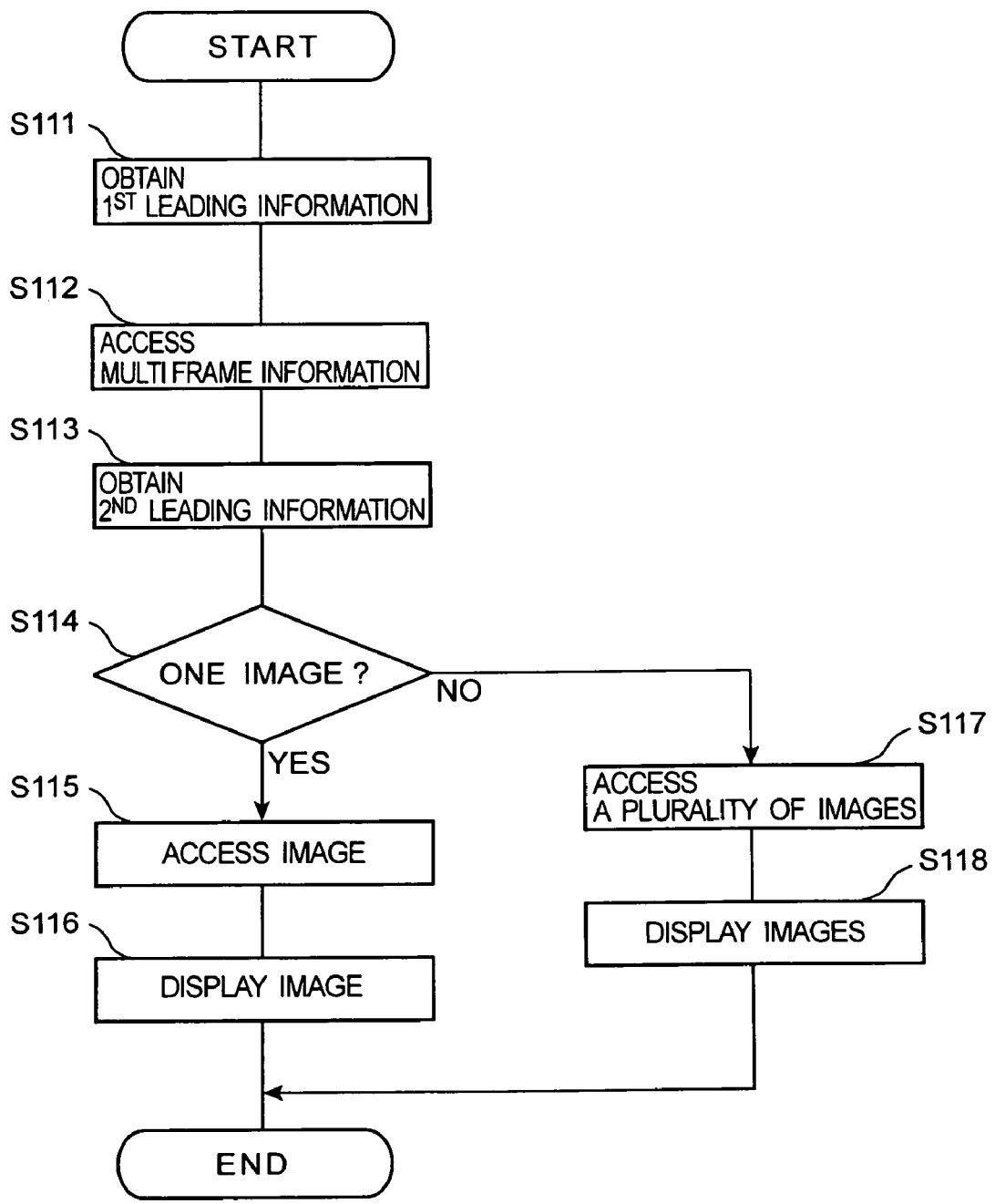
FIG. 11 is a flowchart showing an exemplary flow of an operation of displaying image(s) according to the data format shown in FIGS. 10A and 10B.

FIG. 11 is a flowchart showing an exemplary flow of an operation of displaying image(s) according to the data format shown in FIGS. 10A and 10B. Although FIG. 11 does not show that the controller verifies the patient ID, the controller may verify the patient ID as shown in FIG. 5.

The controller accesses the image-relating information, for example, when an image display has been requested. The controller accesses and obtains the first leading information (step S111). The controller accesses the multiframe information in accordance with the first leading information (step S112). The controller then analyzes the multiframe information and obtains the second leading information included in the multiframe information (step S113). When the image data is for only one image, steps 112 and 113 may be implemented in one step. The controller determines whether the second leading information is for only one image or not (step S114). When the image data is for only one image, the controller may access the image data (the one image) in accordance with the second leading information (step S115) The accessed one image is displayed in the same apparatus or in another apparatus after the accessed image data has been transmitted to another apparatus (step S116). If the image data is for a plurality of images, the controller may access the image data (the plurality of images) in accordance with the second leading information (step S17) The accessed plurality of images are displayed in the same apparatus or in another apparatus after the accessed image data has been transmitted to another apparatus (step S118) The plurality of images may be displayed in parallel. In steps S116 and S118, only the image data transmission may be made instead of the image(s) display.

Recently, an image compression technique called a joint photographic experts group 2000 (hereinafter referred to as JPEG2000) has been introduced. Based on the JPEG2000 technique, internally compressed image data can be extracted from original compressed image data. The internally compressed image data is size-reduced image data, which may be suitable for a low-resolution image display, for example, a display in the PDA 31 or a mobile phone. The original compressed image data can be used for a high-resolution image display, for example, a display in the workstations 15 to 17, and 33.

Figure 12:
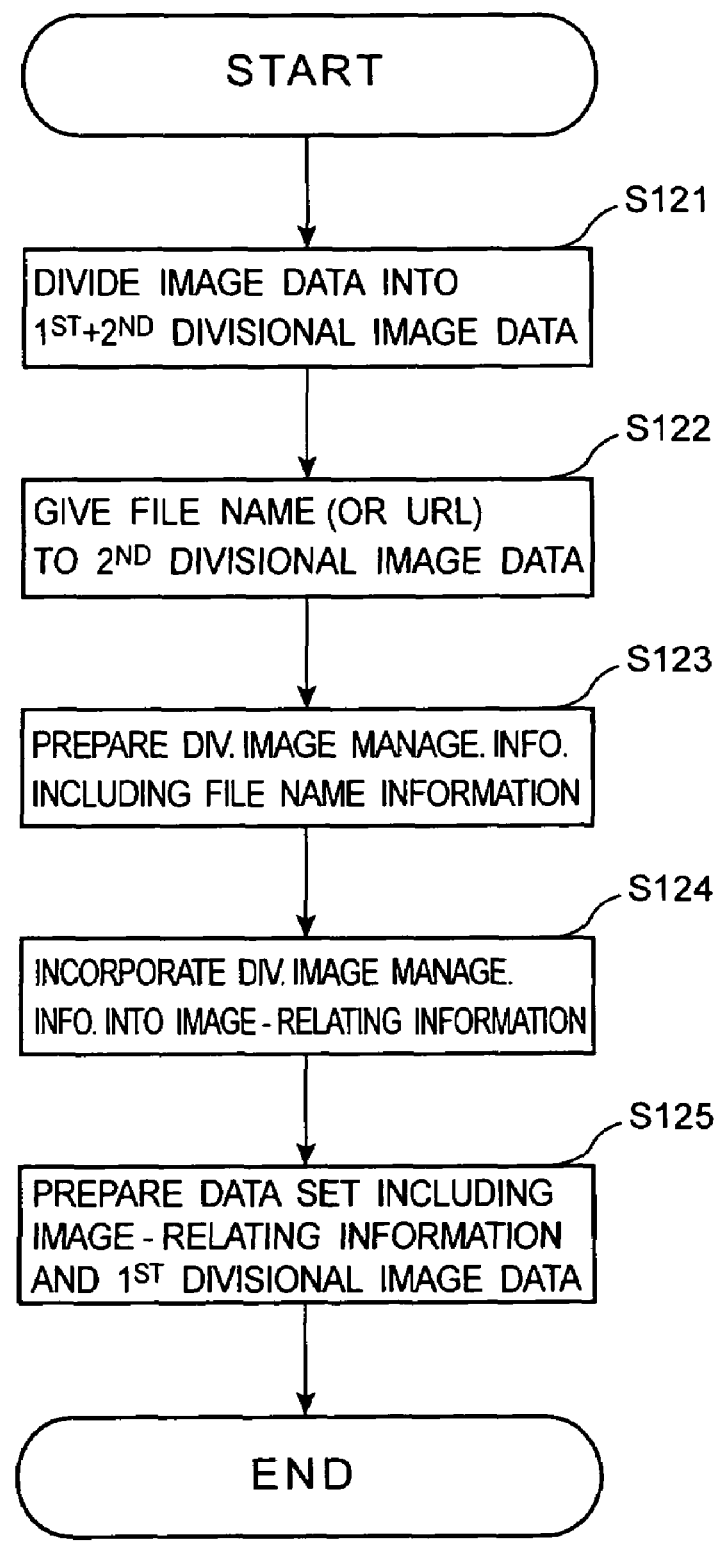
FIG. 12 is a flowchart showing an exemplary flow of preparing a data set including the image-relating information and part of the image data.

Image data such as, for example, the image data compliant with the JPEG2000 may be applied to the embodiments described with reference to FIGS. 2 to 11. One example of preparing image-relating information for the image data compressed in compliance with the JPEG2000 will be described with reference to FIG. 12. The image data can be displayed in phases according to the JPEG2000. FIG. 12 is a flowchart showing an exemplary flow of preparing a data set including the image-relating information and part of the image data. The image compression technique is not limited to the JPEG2000 as long as similar effect is available.

The flow shown in FIG. 12 may be executed by the controller. In FIG. 12, a flow similar to that described for a plurality of images in FIG. 2 may be applied in addition to the flow shown in FIG. 12. The following description pertains to an example that the filing server 11 prepares the image-relating information.

Original image data for one image is divided into two divisional image data (step S121). For example, when the original image data is in a size of 6 mega bites (6 MB), one mega bite (1 MB) of the original image data may be extracted as the first divisional image data. The first divisional image data may be reproduced as a low-resolution image representing a whole part of the original image. Alternatively, the first divisional image data may be reproduced as a high-resolution image representing only specific part of the original image. The rest of the original image data becomes the second divisional image data. The first divisional image data can be made to reproduce a high-resolution whole image with the second divisional image data.

The second divisional image data is given a file name or a URL (a uniform resource locator) as link information (step S122). For example, if the patient ID is '1.2.80.56.99.0', this patient ID may be used as the file name. The file name may alternatively be a user ID of the patient. The URL may be prepared by combining an IP (internet protocol) address or a domain name of the filing server 11, the patient ID or the user ID, and a hash value of the patient ID or the user ID. For example, if the IP address is '192.168.1.1' and the hash value is '501', the URL may become 'http://192.168.1.1/1.2.80.56.99.0.dcm?hash check=501'. Characters showing a name of the patient such as, for example, 'Taro Yamada', a date of birth such as, for example, '01.01.2000', a sex such as, for example, 'male', or any other information to specify the patient may be added to the patient ID or the user ID.

The controller prepares divisional image management information of the divisional image data (step S123). The divisional image management information may include each image data size of the first and second divisional image data, and the number of divisional image data. The file name of the URL given in step S122 is also included in the divisional image management information. The prepared divisional image management information is incorporated into the image-relating information (step S124). The prepared divisional image management information may be incorporated as information corresponding to the multiframe information.

The controller then prepares the second leading information leading to the first divisional image data and incorporates the prepared second leading information into the image-relating information and places it around the divisional image management information. The controller also prepares the first leading information leading to the second leading information or the divisional image management information. The first leading information may include, for example, an offset value. The first leading information and the second leading information may be prepared in a manner similar to those described for FIG. 2. The controller prepares a data set including the image-relating information and the first divisional image data following the image-relating information (step S125).

Figure 13:
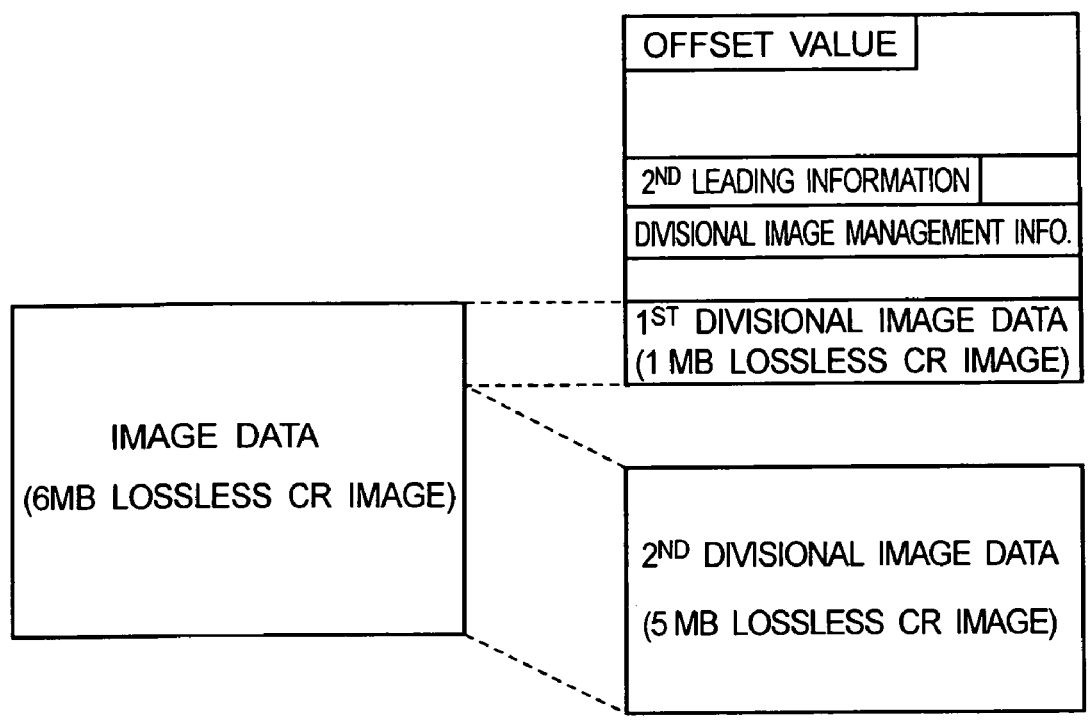
FIG. 13 is an illustration showing an example of a data format of the data set prepared in accordance with the flowchart shown in FIG. 12.

FIG. 13 is an illustration showing an example of a data format of the data set prepared in accordance with the flowchart shown in FIG. 12. As shown in FIG. 13, the original image data is, for example, six (6) mega-byte lossless CR (computed radiography) image data. The CR image may be generated by the DR apparatus 14. One (1) mega-byte lossless CR image data is accompanied by the image-relating information as the first divisional image data of the original image data. Five (5) mega-byte lossless CR image data is prepared as the second divisional image data which is an object different from the data set or is not part of the data set although the second divisional image data is related or linked to the divisional image management information in the image-relating information. In the image-relating information, the offset value as the first leading information may be placed at its head.

In the example shown in FIG. 13, the second leading information is placed ahead of the divisional image management information. In this case, the first leading information may lead to the second leading information and the controller continues to analyze the image-relating information until the divisional image management information. After the analysis of the divisional image management information, the controller may access the first divisional image data. If the divisional image management information is placed ahead of the second leading information in the image-relating information, the first leading information may lead to the divisional image management information and the controller continues to analyze the image-relating information until the second leading information. After the analysis of the second leading information, the controller may access the first divisional image data.

While an image is displayed based on the first divisional image data, the controller may control to display a button or the like to display an original image based on the original image data. The button or the like may alternatively be prepared and displayed regularly. The button or the like may relate to the file name or the URL. In response to the doctor's instruction to the button or the like, the controller accesses the second divisional image data on the basis of the file name or the URL so that the complete (6 MB) original image can be reproduced and displayed.

In this example, when the PDA 31 is not capable of displaying the original image because the size of the image data is too large for the PDA 31, the PDA 31 can only receive the data set without requesting the second divisional image data and display the low resolution image in its display.

When the workstations 15 to 17 or 33 which may be capable of displaying the original image receive the data set and then the second divisional image data, the workstations 15 to 17 or 33 can verify the agreement between the data set and the second divisional image data. In other words, the controller provided in the workstations 15 to 17 or 33 can verify that the patient ID or the user ID included in the file name or the URL is correct by comparing to the patient ID included in the image-relating information.

Further, the controller may compare a hash value calculated based on the patient ID or the user ID to the hash value which is part of the URL so as to see the right of the patient ID or the user ID included in the URL. This may be useful to avoid transmitting or receiving the second divisional image data inappropriately. If the patient ID or the user ID included in the URL which is incorporated in the divisional image management information had been tampered, the second divisional image data would be requested to transmit (or transfer) based on the wrong URL. Also, if memory crash or network instability occurred, the URL included in a transmission request of the second divisional image data might be caused to change during the transmission. In these cases, the hash value calculated based on the patient ID or the user ID included in the URL may become different from the hash value included in the URL.

Therefore, if the controller determines that the patient ID or the user ID is wrong by the comparison, the controller may stop transmitting the second divisional image data.

Figure 14:
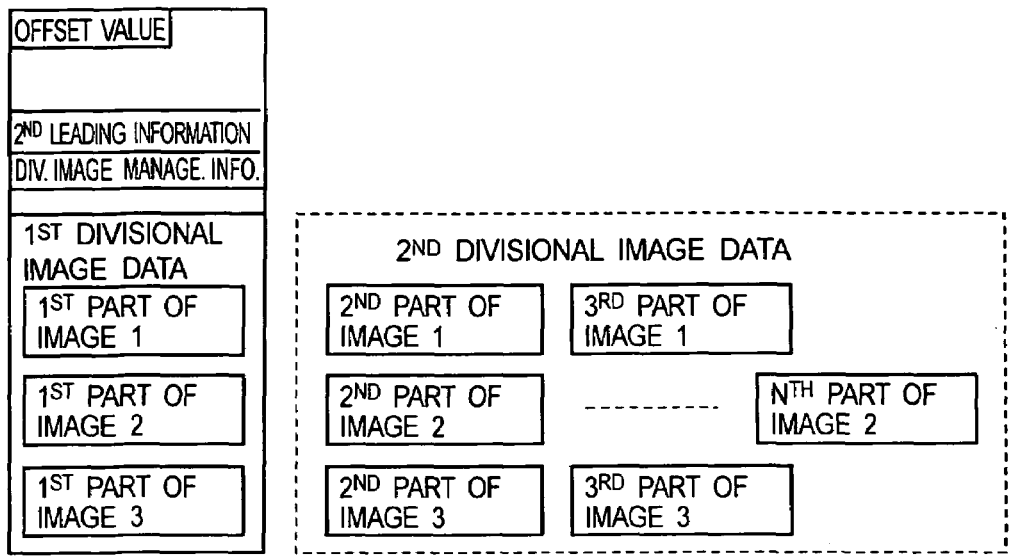
FIG. 14 is an illustration showing an example of the first and second divisional image data when the image data is for a plurality of images.

When the image data is for a plurality of images, each of the plurality of images may be divided into two or more divisional image data. FIG. 14 is an illustration showing an example of the first and second divisional image data when the image data is for a plurality of images. As shown in FIG. 14, the image data accompanied by the image-relating information includes the first divisional image data. The first divisional image data may include the first divisional image data of an image 1 (or the first part (e.g., 0.5 MB) of the image 1 (e.g., 1.5 MB)), the first divisional image data of an image 2 (or the first part of the image 2) and the first divisional image data of an image 3 (or the first part of the image 3). The second divisional image data includes the rest part of each image. With respect to the images 1 and 3, the second part (e.g., 0.5 MB) and the third part (e.g., 0.5 MB) may be included as divisional image data in the second divisional image data. With respect to the image 2, the second to the Nth parts may be included as divisional image data in the second divisional image data. Each of those parts is linked to the divisional image management information.

Even when the image data is for a plurality of images, the first phase of each image included in the data set can be displayed relatively soon and the rest may be displayed in two or N−1 phases in accordance with the second divisional image data. Accordingly, since the doctor may not have to wait for the initiation of the image display for a long time as before, the doctor may not be so worried or irritated.

The image-relating information may be formed in a manner similar to that shown in FIG. 13. Herein, however, the second leading information leads to the first part of the image 1, the first part of the image 2, and the first part of the image 3. The divisional image management information includes file names or URLs corresponding to the parts of the images 1, 2, and 3 and treats the parts of the images 1, 2, and 3 as individual objects or objects different from the data set. Each of the file names or the URLs may include a frame number, a divisional number, or information indicating which part of each image (1, 2, or 3) it is. The divisional image management information may also include an image data size of the each part and the number of parts divided for each image (1, 2, or 3).

According to the embodiment explained with reference to FIGS. 12 and 14, the data set and the second divisional image data can be transmitted (or transferred) as different objects, respectively. Therefore, the image can be displayed in phases based on the first and second divisional image data even when the data set and the second divisional image data are transmitted in a protocol such as, for example, HTTP (HyperText Transfer Protocol)/1.0. This means, even if the workstations 15, 16, 33, or the PDA 31 corresponds to HTTP/1.0 but not HTTP/1.1, the image can be transmitted individually and displayed in phases. On the other hand, when the image data is not prepared in the divisional manner as explained with reference to FIGS. 2 to 11, the image may be transmitted individually and displayed in phases only when the data set is transmitted (or transferred) in a protocol with an offset transfer technique such as, for example, HTTP/1.1.

Figure 15:
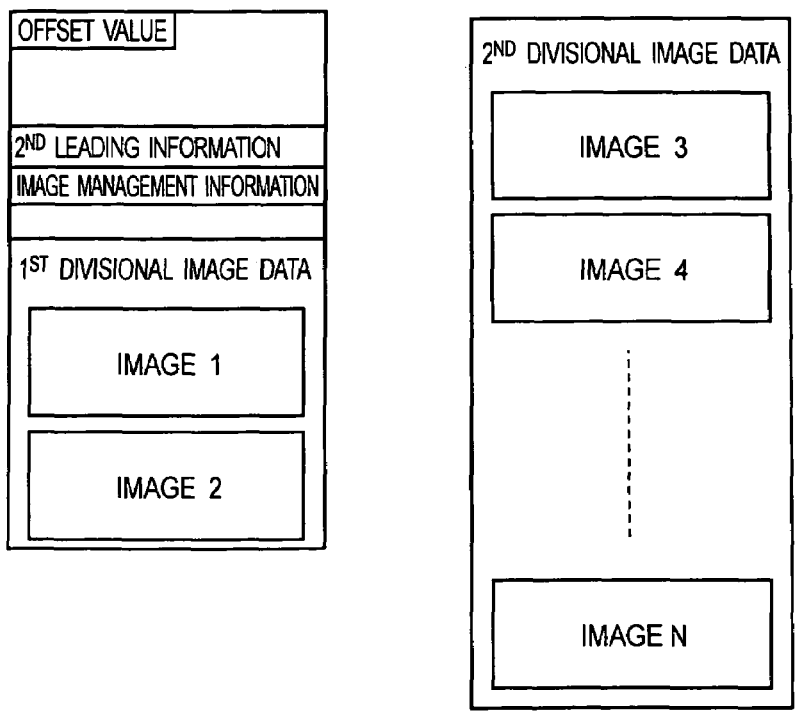
FIG. 15 is an illustration showing another example of the first and second divisional image data when the image data is for a plurality of images.

Instead of dividing the image data with respect to each image, the image data may be divided with respect to a plurality of images. When a plurality of (or a series of) (e.g., N) images are generated, the image data accompanied by the image-relating information may be for only images 1 and 2 as the first divisional image data as shown in FIG. 15. Images 3 to N may be prepared as the second divisional image data and are linked to the divisional image management information included in the image-relating information. Accordingly, the images 1 and 2 can be displayed without waiting for obtaining the rest of the images. This can be advantageous of reducing time to display the image 1 (and the image 2) and avoiding the doctor from being worried or irritated.

In the verification described above, any other information than those mentioned above may be used. In addition, for example, when the second divisional image data is prepared with the file name or the URL which includes a patient name, a date of birth, and/or a sex, the file name or the URL can be displayed for the doctor. The doctor can see whether or not the patient identified by the image-relating information is identical to the patient identified by the file name or the URL. That is, the doctor can see whether the obtained data set and the obtained second divisional image data are for the same patient or not.

The number of divisional image data is not limited to two but may be more according to the necessity.

The embodiments have been described with respect to an application to the medical field. However, similar data preparation and the like may be applied to other fields in which image data is required to be stored and/or transmitted through a network.

In the above embodiments, the filing server 11, the CT apparatus 12, the MRI apparatus 13, the DR apparatus, the workstation 15, 16, 17, and/or 33, the PDA 31, the router 19, and/or 32 may have a random access memory (RAM), which can receive and store computer programs and applications as computer readable instructions in a temporary and/or non-volatile state. The above one or more apparatuses or the like may further have a hard disk drive as part of the controller for reading from and writing to a hard disk, a magnetic disk drive for reading from and writing to a magnetic disk, and/or an optical disk drive for reading from and writing to an optical disk (such as a CD, CDR, CD-RW, DVD, or other optical device). Those skilled in the art will appreciate that one or more of such memory, drives, and their respective media are examples of a computer readable medium for storing computer readable instructions, which when executed, may implement an embodiment of the present invention.

The embodiments of the present invention described above are examples described only for making it easier to understand the present invention, and are not described for the limitation of the present invention. Consequently, each component and element disclosed in the embodiments of the present invention may be redesigned or modified to its equivalent within a scope of the present invention. Furthermore, any possible combination of such components and elements may be included in a scope of the present invention as long as an advantage similar to those obtained according to the above disclosure in the embodiments of the present invention is obtained.

Numerous modifications and variations of the present invention are possible in light of the above teachings. It is therefore to be understood that within the scope of the appended claims, the invention may be practiced otherwise than as specifically described herein.

The invention claimed is:

1. An image storing apparatus for storing image data for at least one image generated by an imaging apparatus, the image storing apparatus comprising:
   a receiving unit configured to receive the image data;
   a processor configured to prepare image-relating information and prepare a data set including the image-relating information and the image data following the image-relating information, wherein the processor prepares leading information leading to the image data as part of the image-relating information; and
   a storage device configured to store the data set,
   wherein the leading information is prepared based on a size of the image-relating information.

2. The apparatus according to claim 1, wherein the leading information is placed at a head of the image-relating information.

3. The apparatus according to claim 1, wherein the leading information is placed ahead of patient identification information.

4. The apparatus according to claim 1, wherein the leading information is placed within a first one tenth of the image-relating information in size.

5. The apparatus according to claim 1, further comprising a controller configured to access the image-relating information and access the image data based on the leading information.

6. The apparatus according to claim 5, wherein the controller accesses the image data without analyzing other information of the relating information placed behind the leading information.

7. The apparatus according to claim 5, wherein the controller accesses the image data after analyzing at least patient identification information.

8. The apparatus according to claim 1, wherein, when the image data is for a plurality of images, the leading information leads to a first of the plurality of images.

9. The apparatus according to claim 1, wherein, when the image data is for a plurality of images, the leading information leads to one or more of the plurality of images.

10. The apparatus according to claim 1, wherein the leading information includes first leading information leading to second leading information and the second leading information leading to one image when the image data is for the one image and one or more of a plurality of images when the image data is for the plurality of images.

11. The apparatus according to claim 10, wherein the second leading information is included in multiframe information when the image data is for the plurality of images.

12. The apparatus according to claim 1, wherein the leading information includes first identification information indicating that the image data is for one image and direct-leading information leading to the image data.

13. The apparatus according to claim 1, wherein data for each of the at least one image is divided into two or more parts.

14. The apparatus according to claim 13, wherein the image data is compressed in compliance with a joint photographic experts group 2000.

15. The apparatus according to claim 13, wherein, when the image data is for one image, the data set includes a first part of the image data, the first part corresponding to one of the divided parts of the data for the one image.

16. The apparatus according to claim 15, wherein a rest of the image data is prepared as at least one object different from the data set.

17. The apparatus according to claim 16, wherein the image-relating information includes link information linking to the rest of the image data.

18. The apparatus according to claim 16, wherein the rest of the image data is divided into a plurality of parts corresponding to the divided two or more parts of the one image.

19. The apparatus according to claim 1, wherein, when the receiving unit receives the image data for a series of N images, the data set includes part of the image data which is for less than N images.

20. The apparatus according to claim 19, wherein a rest of the image data which is for a rest of the N images is prepared as at least one object different from the data set.

21. The apparatus according to claim 1, wherein the leading information is prepared based on a size of part of the image-relating information between first and second predetermined information included in the image-relating information.

22. An image storing apparatus for storing image data for at least one image generated by an imaging apparatus, the image storing apparatus comprising:
a receiving unit configured to receive the image data;
a processor configured to prepare image-relating information and prepare a data set including the image-relating information and the image data following the image-relating information, wherein the processor prepares leading information leading to the image data as part of the image-relating information; and
a storage device configured to store the data set,
wherein the leading information includes first identification information indicating that the image data is for a plurality of images and first leading information leading to multiframe information, and the multiframe information is included in the image-relating information and includes second leading information leading to one or more of the plurality of images.

23. The apparatus according to claim 22, wherein the multiframe information is placed behind other information of the relating information.

24. The apparatus according to claim 22, wherein the leading information is prepared based on a size of the image-relating information.

25. An image storing apparatus for storing image data for at least one image generated by an imaging apparatus, the image storing apparatus comprising:
a receiving unit configured to receive the image data;
a processor configured to prepare image-relating information and prepare a data set including the image-relating information and the image data following the image-relating information, wherein the processor prepares leading information leading to the image data as part of the image-relating information; and
a storage device configured to store the data set,
wherein data for each of the at least one image is divided into two or more parts, and
wherein, when the image data is for a plurality of images, the data set includes a first part of first data of the image data and a second part of second data of the image data, the first data being for a first of the plurality of images, the second data being for a second of the plurality of images, the first part corresponding to one of the divided parts of the data for the first image, and the second part corresponding to one of the divided parts of the data for the second image.

26. The apparatus according to claim 25, wherein the leading information is prepared based on a size of the image-relating information.

27. An image display apparatus for displaying at least one image based on an image data generated by an imaging apparatus, the image display apparatus comprising:
a receiving unit configured to receive the image data; and
a processor configured to prepare image-relating information and prepare a data set including the image-relating information and the image data following the image-relating information,
wherein the processor prepares leading information leading to the image data as part of the image-relating information; and a display configured to display the at least one image in accordance with the leading information and the image data, and
wherein the leading information is prepared based on a size of the image-relating information.

28. An imaging apparatus for generating an image data for at least one image, comprising:
an image generating unit configured to generate the image data; and
a processor configured to prepare image-relating information and prepare a data set including the image-relating information and the image data following the image-relating information,
wherein the processor prepares leading information leading to the image data as part of the image-relating information, and
wherein the leading information is prepared based on a size of the image-relating information.

29. An information processing apparatus, comprising:
a receiving unit configured to receive an image data for at least one image;
a processor configured to prepare image-relating information and prepare a data set including the image-relating information and the image data following the image-relating information, wherein the processor prepares leading information leading to the image data as part of the image-relating information; and
an output unit configured to output the data set,
wherein the leading information is prepared based on a size of the image-relating information.

30. A computer readable medium on which is stored a program module for preparing a data set, the program module comprising instructions, which when executed perform steps comprising:
preparing leading information which leads to an image data for at least one image, the image data being included in the data set;
preparing image-relating information including the leading information; and
preparing the data set including the image-relating information and the image data following the image-relating information,
wherein the leading information is prepared based on a size of the image-relating information.

* * * * *